US00PP13731P39

(12) United States Plant Patent
Pieters

(10) Patent No.: US PP13,731 P3
(45) Date of Patent: Apr. 22, 2003

(54) CHRYSANTHEMUM PLANT NAMED 'GEDI ONE SAP'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,494

(22) Filed: Jun. 4, 2001

(65) Prior Publication Data

US 2002/0188980 P1 Dec. 12, 2002

(51) Int. Cl.[7] ..... A01H 5/00
(52) U.S. Cl. ..... Plt./290
(58) Field of Search ..... Plt./290, 287, 286, Plt./296

(56) References Cited

U.S. PATENT DOCUMENTS

PP10,216 P 1/1998 Pieters ..... Plt./290
PP10,219 P 1/1998 Pieters ..... Plt./296

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, bronze ray florets, very uniform round growth habit, and a large quantity of blooms per flowering branch.

1 Drawing Sheet

LATIN NAME

*Dendranthema morifolium.*

VARIETY

Figure 1:
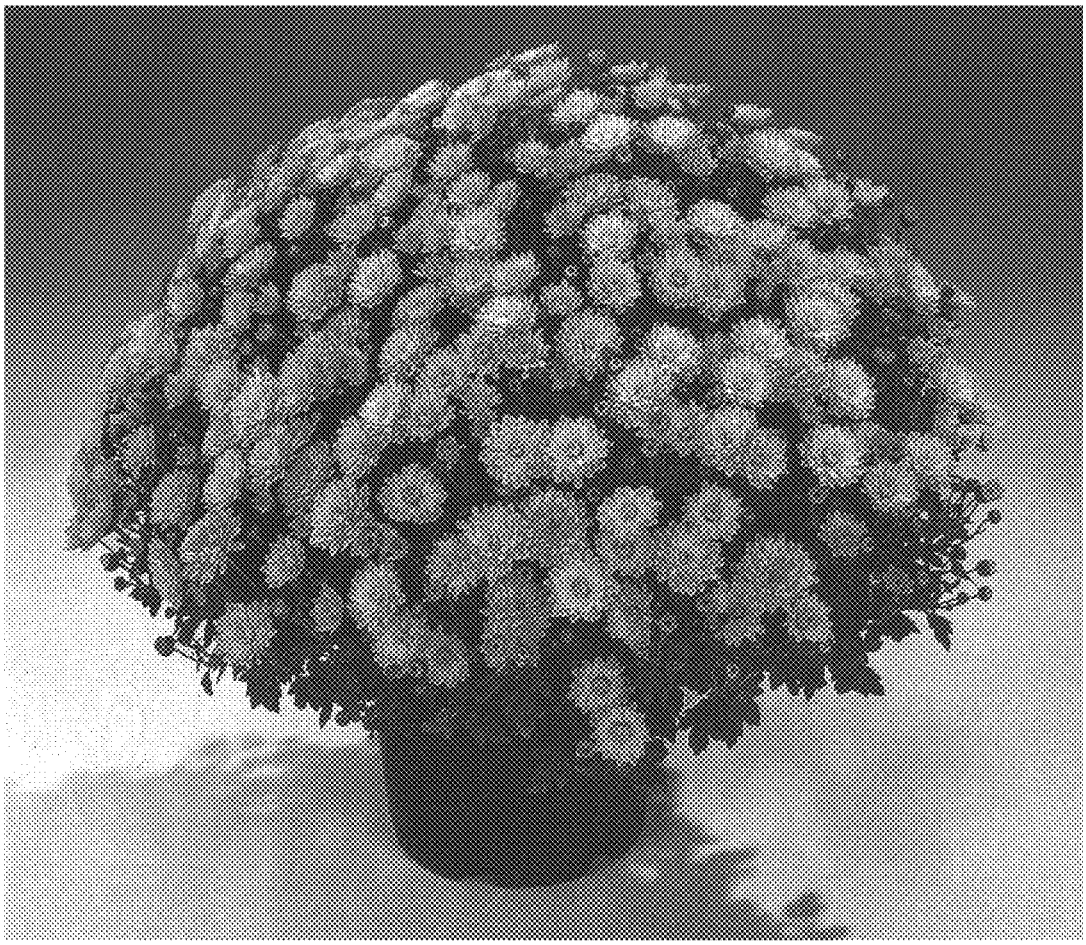

'GEDI ONE SAP'.

BACKGROUND OF THE INVENTION

The present invention relates to a new and distinct cultivar of Chrysanthemum plant, herein after referred to by the cultivar name 'GEDI ONE SAP'.

This new cultivar was the result of hybridization of a female parent, 'Cobra' (U.S. Plant Pat. No. 10,219) with a male parent, 'Pink Elani' (unpatented). The new cultivar was discovered by the inventor in October 1995.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE SAP' has not been observed under all possible environmental conditions. The phenotype may vary somewhat with variations in environment such as temperature, daylength, and light intensity, without, however, any variance in genotype.

The following traits have been repeatedly observe and are determined to be the unique characteristics of 'GEDI ONE SAP.' These characteristics in combination distinguish 'GEDI ONE SAP' as a new and distinct Chrysanthemum:

1. Decorative type inflorescence;
2. Consistent flowering response to short days, blooming consistently after 49 days of short day length;
3. Free branching habit;

4. Bronze ray florets;
5. Very uniform round growth habit; and
6. Large quantity of blooms per flowering branch.

Plants of the new Chrysanthemum are similar to plants of the parent cultivars in most horticultural characteristics, however plants of the new cultivar differ from plants of the female parent cultivar 'Cobra' in the following characteristics:

1. The new cultivar has more blooms per flowering branch;
2. The new cultivar naturally blooms 3 weeks later;
3. The new cultivar has a different bloom type; and
4. The new cultivar has smaller diameter flowers.

The new cultivar also differed from the male parent 'Pink Elani' in the following characteristics:

1. The new cultivar has an different ray color; and
2. The new cultivar has a different flower type.

The new cultivar can be compared to the Chrysanthemum cultivar 'Aldo' (disclosed in U.S. Plant Pat. No. 10,216). However plants of the new Chrysanthemum differed from the plants of the cultivar 'Aldo' in the following characteristics:

1. New cultivar naturally blooms approximately 2 weeks later;
2. New cultivar has more ray florets;
3. New cultivar has a more round plant shape and greater branching; and
4. New cultivar has more blooms per flowering branch.

BRIEF DESCRIPTION OF THE PHOTOGRAPHS

The photograph shows a plant of 'GEDI ONE SAP' grown in a 2-gallon container. A single cutting was used in the container. It was planted in mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 130 days from rooted cutting. The growing conditions range from 60° to 65° F. at night to 70° to 85° F. during the day. Measurements and numerical values represent averages of typical flowering types.

Botanical classification: *Dendranthema morifolium* cultivar 'GEDI ONE SAP'
Commercial classification: Garden-type Chrysanthemum
Parentage: Hybridization of female parent 'Cobra' and male parent 'Pink Elani'

PROPAGATION

Time to rooting: 7 to 14 days at approximately 21° C.
Root description: Fine, fibrous

PLANT

Growth habit: Mounding herbaceous perennial
Height: Approximately 22 cm
Growth rate: Moderate
Plant spread: Approximately 23 cm
Branching characteristics: Free Branching
Length of lateral branches: Approximately 24 cm
Number of leaves per lateral branch: Approximately 27
Stem color: Near 137A

FOLIAGE

Leaf:
- *Arrangement.*—Alternate, single.
- *Average Length.*—Approximately 6.8 cm.
- *Average width.*—Approximately 3.9 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—young foliage upper side: Near 137A young foliage under side: Near 137A mature foliage upper side: Near 137A mature foliage under side: Near 137A venation upper side: Near 137C venation under side: Near 137C.

Petiole:
- *Average length.*—Approximately 2.5 cm.
- *Color.*—Near 138A.
- *Diameter.*—2 mm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first two weeks of October.
- *Number of inflorescences per stem.*—Approximately 17.
- *Inflorescence diameter.*—Approximately 5.1 cm.
- *Inflorescence depth.*—1.5 cm.
- *Inflorescence longevity on plant.*—Approximately 22–26 days.
- *Persistence.*—Persistent.

Ray florets:
- *Appearance.*—Matte.
- *Texture.*—Smooth.
- *Average number per flower.*—200.
- *Shape.*—Oblanceolate.
- *Margin.*—Entire.
- *Apex.*—Obtuse.
- *Length.*—Approximately 2.8 cm.
- *Width.*—Approximately 0.8 cm.
- *Color.*—upper surface at first opening: Near 168B upper surface at maturity: Near 24B upper surface at fading: Near 23C under surface at first opening: Near 25B under surface at maturity: Near 26A under surface at fading: Near 23B.

Disc florets:
- *Appearance.*—Shiny.
- *Texture.*—Smooth.
- *Average number per flower.*—Approximately 60.
- *Shape.*—Cylindric.
- *Apex.*—Obtuse.
- *Average length.*—Approximately 1 cm.
- *Average width.*—Approximately 0.2 cm.
- *Color.*—at first opening: Near 2A at maturity: Near 21A at fading: Near 17D.

Peduncle:
- *Length.*—at terminal end (shortest): Approximately 5 cm at lateral end (longest): Approximately 11 cm.
- *Strength.*—Moderate.
- *Color.*—Near 137C.
- *Habit.*—Erect.
- *Surface texture.*—Lightly pubescent.

Inflorescence bud:
- *Length.*—Approximately 1 cm.
- *Diameter.*—Approximately 1 cm.
- *Form.*—Globular.
- *Color.*—Near 168A.

Phyllaries:
- *Appearance.*—Matte.
- *Texture.*—Lightly pubescent.
- *Number.*—Approximately 40 to 50.
- *Shape.*—Ovate.
- *Margin.*—Entire.
- *Apex.*—Acute.
- *Diameter.*—0.2 cm.
- *Length.*—0.3 cm.
- *Color.*—upper side: Near 137A under side: Near 137A.

REPRODUCTIVE ORGANS

Ray florets:
- *Number of pistils per flower.*—1.
- *Stigma shape.*—2 branched.
- *Stigma color.*—Near 17A.
- *Style color.*—Near 17D.
- *Style length.*—0.5 cm.
- *Stamens.*—Absent.

Disc florets:
- *Number of pistils per flower.*—1.
- *Stigma shape.*—Cylindric.
- *Style length.*—0.5 cm.
- *Number of stamens per flower.*—Approximately 5.
- *Anther shape.*—Tubular.

*Anther color.*—Near 16A.
*Pollen color.*—Near 17B.

OTHER CHARACTERISTICS

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct variety of Chrysanthemum plant named 'GEDI ONE SAP' as herein illustrated and described.

* * * * *